(12) United States Patent
Coupard et al.

(10) Patent No.: US 9,725,376 B2
(45) Date of Patent: Aug. 8, 2017

(54) PROCESS FOR DEHYDRATION OF ETHANOL INTO ETHYLENE USING PRETREATMENT OF THE FEEDSTOCK

(71) Applicants: IFP ENERGIES NOUVELLES, Rueil-Malmaison (FR); TOTAL RESEARCH & TECHNOLOGY FELUY, Seneffe (BE)

(72) Inventors: Vincent Coupard, Villeurbanne (FR); Natacha Touchais, Vienne (FR); Thomas Plennevaux, Lyons (FR); Emilie Kobel, Chasse sur Rhone (FR); Stephanie Fleurier, Lyons (FR); Walter Vermeiren, Houthalen-Helchteren (BE); Delphine Minoux, Nivelles (BE); Philip De Smedt, Sint-Niklaas (BE); Cindy Adam, Wierde (BE); Nikolai Nesterenko, Nivelles (BE)

(73) Assignees: IFP Energies Nouvelles, Rueil-Malmaison (FR); Total Research & Technology Feluy, Seneffe (BE)

( * ) Notice: Subject to any disclaimer, the term of this patent is extended or adjusted under 35 U.S.C. 154(b) by 15 days.

(21) Appl. No.: 14/647,174

(22) PCT Filed: Nov. 18, 2013

(86) PCT No.: PCT/FR2013/052768
§ 371 (c)(1),
(2) Date: May 26, 2015

(87) PCT Pub. No.: WO2014/083261
PCT Pub. Date: Jun. 5, 2014

(65) Prior Publication Data
US 2015/0291485 A1 Oct. 15, 2015

(30) Foreign Application Priority Data
Nov. 27, 2012 (FR) .................................... 12 03200

(51) Int. Cl.
| C01C 1/24 | (2006.01) |
| C07C 1/24 | (2006.01) |
| C07C 29/76 | (2006.01) |
| C07C 41/09 | (2006.01) |

(52) U.S. Cl.
CPC ................ *C07C 1/24* (2013.01); *C07C 29/76* (2013.01); *C07C 41/09* (2013.01); *C07C 2527/173* (2013.01); *C07C 2529/40* (2013.01); *C07C 2529/85* (2013.01)

(58) Field of Classification Search
CPC .. C07C 1/00; C07C 1/24; C07C 29/76; C07C 41/09; C07C 11/04; C07C 31/08; C07C 43/06; C07C 2527/173; C07C 2529/40; C07C 2529/85
USPC .................................. 585/638, 639, 640, 641
See application file for complete search history.

(56) References Cited

U.S. PATENT DOCUMENTS

| 3,095,458 | A | * | 6/1963 | Judice ..................... C07C 29/06 558/39 |
| 4,396,789 | A | * | 8/1983 | Barrocas ................... C07C 1/24 585/639 |
| 9,000,236 | B2 | | 4/2015 | Minoux et al. |
| 9,085,502 | B2 | * | 7/2015 | Coupard ................... C07C 1/24 585/639 |
| 2011/0313213 | A1 | | 12/2011 | Minoux et al. |
| 2013/0190547 | A1 | | 7/2013 | Coupard et al. |

FOREIGN PATENT DOCUMENTS

| FR | 2978145 A1 | 1/2013 |
| WO | 2010060981 A1 | 6/2010 |

OTHER PUBLICATIONS

International Search Report dated Apr. 28, 2014 issued in corresponding PCT/FR2013/052768 application (pp. 1-2).

* cited by examiner

*Primary Examiner* — Sharon Pregler
(74) *Attorney, Agent, or Firm* — Millen White Zelano & Branigan, P.C.

(57) ABSTRACT

The invention relates to a process for dehydration of an ethanol feedstock into ethylene comprising at least the stages:
a) A stage for pretreatment of the ethanol feedstock on an acidic solid,
b) A stage for evaporation of said pretreated ethanol feedstock in a heat exchanger,
c) A stage for superheating said evaporated feedstock in such a way as to bring it to an inlet temperature that is compatible with the temperature of a dehydration reaction,
d) A stage for dehydration of said feedstock that is obtained from stage c) in at least one adiabatic reactor that contains at least one dehydration catalyst.

14 Claims, 1 Drawing Sheet

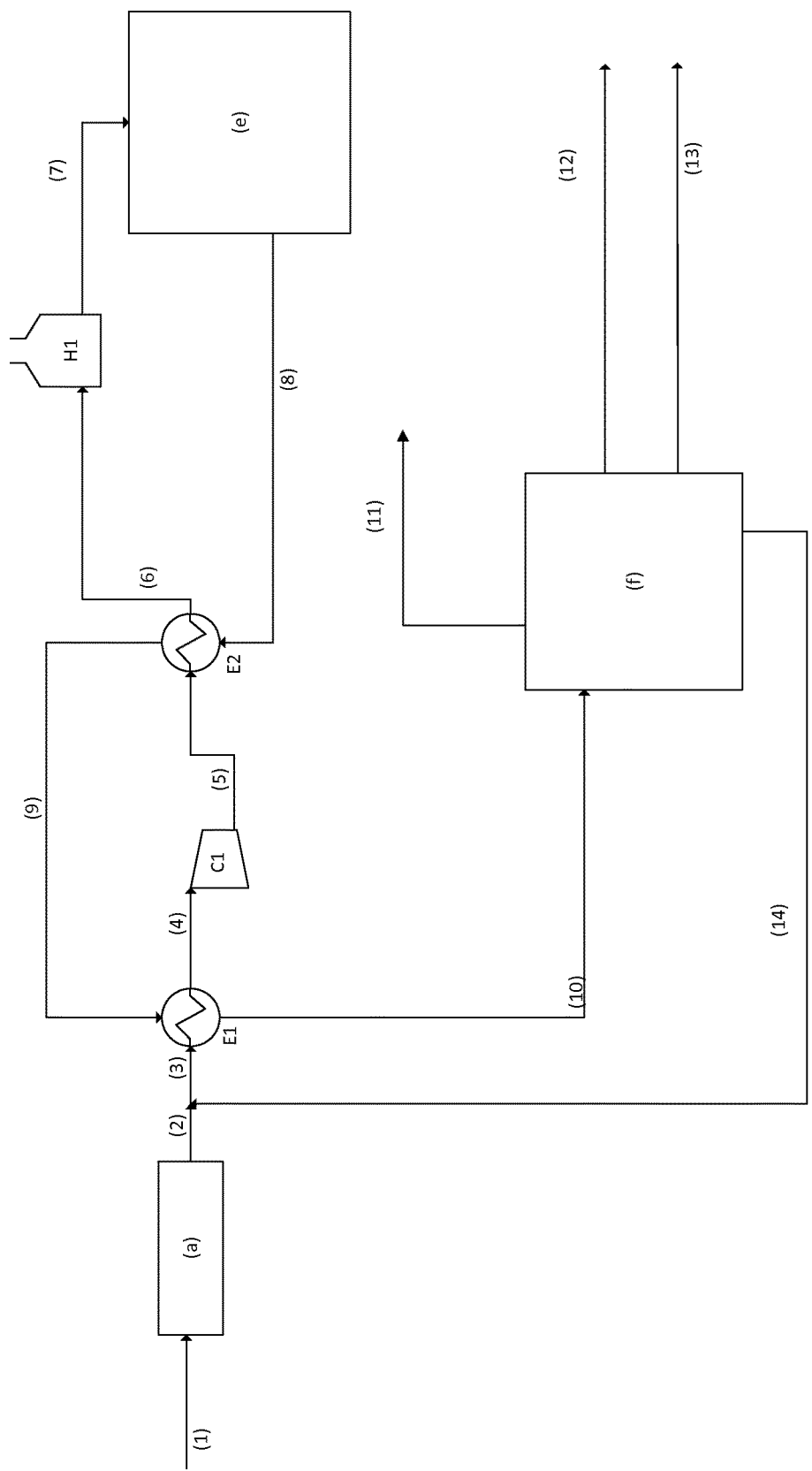

PROCESS FOR DEHYDRATION OF ETHANOL INTO ETHYLENE USING PRETREATMENT OF THE FEEDSTOCK

FIELD OF THE INVENTION

This invention relates to a process for transformation of ethanol into ethylene and in particular to a process for dehydration of ethanol.

PRIOR ART

The reaction of dehydration of ethanol into ethylene is known and has been presented in detail since the end of the 19th century. "The Dehydration of Alcohols over Alumina. I: The Reaction Scheme," H. Knözinger, R. Köhne, Journal of Catalysis (1966), 5, 264-270 is considered to be the basic publication on the works on dehydration of alcohols, including ethanol. It is known that this reaction is very endothermic, balanced, and shifted toward ethylene at high temperature. The temperature drop that corresponds to the total conversion of pure ethanol in an adiabatic reactor is 380° C. At a lower temperature, ethanol is converted into diethyl ether (DEE). This reaction "intermediary" can be present in processes for dehydration of ethylene in which the conversion is partial or between two reactors in multi-reactor processes. The DEE can then be converted into ethylene at a higher temperature. The reference catalyst that is often used is a monofunctional acid catalyst, with the gamma-alumina being the most cited catalyst. The zeolites are also used for this application, in particular the ZSM5 from the 1980s, such as, for example, in "Reactions of Ethanol over ZSM-5," S. N. Chaudhuri & al., Journal of Molecular Catalysis 62: 289-295 (1990).

The U.S. Pat. No. 4,232,179 describes a process for dehydration of ethanol into ethylene in which the heat that is necessary to the reaction is supplied by the introduction into the reactor of a coolant mixed with the feedstock. The coolant is either water vapor that is obtained from an outside source, or an outside stream that comes from the process, or the recycling of a portion of the effluent from the dehydration reactor, i.e., the ethylene that is produced. The introduction of the mixture of the feedstock with said coolant makes it possible to provide the heat that is necessary for keeping the temperature of the catalytic bed at a compatible level with the desired conversions. In the case where the coolant is the effluent from the dehydration reactor, a compressor for recycling said effluent is necessary. However, the recycling of the ethylene that is produced by the reaction is a drawback because the introduction of ethylene modifies the balance of the dehydration reaction. In addition, the ethylene participates in secondary oligomerization reactions, transfer of hydrogen and disproportionation of olefins that are reactions of an order that is higher than 0 relative to their reagent. The increase in the ethylene concentration from the beginning of the reaction multiplies the formation of secondary products. The loss of ethylene is therefore more significant, which is reflected by a lowering of selectivity.

The patent application WO 2007/134415 describes a process for dehydration of ethanol into ethylene that is improved relative to that of U.S. Pat. No. 4,232,179 that makes possible a reduced investment cost, owing to a reduced number of pieces of equipment and a reduced operating cost, owing to the non-use of water vapor external to the process. In this process, at least a portion of the effluent from the dehydration reactor (mixture of ethylene that is produced and water vapor) and the superheated water vapor obtained from the water that is produced by the dehydration of ethanol and condensed in the reactor are used as a coolant and enter into the dehydration reactor by mixing with ethanol. Said patent application is silent on the pressure condition that is to be observed between the ethanol feedstock and the effluent for the purpose of maximizing the heat exchange.

The U.S. Pat. No. 4,396,789 also describes a process for dehydration of ethanol into ethylene in which the ethanol and the water vapor acting as coolant are introduced into the first reactor at a temperature of between 400 and 520° C. and at a high pressure of between 20 and 40 atm, in such a way that the effluent that is produced by the dehydration reaction is drawn off from the last reactor at a pressure that is at least higher than 18 atm, with said reaction product, i.e., ethylene, being able to undergo, after cooling, the final cryogenic distillation stage without an intermediate compression stage. Said process is also characterized by a heat exchange between said product of the dehydration reaction and the feedstock that is introduced into the first reactor, said reaction product being used for evaporating the feedstock that enters into the first reactor. The unconverted ethanol, at least a portion of the water that is formed during the reactions of the process, and the water that is added for the final washing of gases are recycled to ensure the complete conversion of the ethanol.

The patent application WO 2011/002699 discloses a process for dehydration of an ethanol feedstock into ethylene comprising the evaporation of a mixture of ethanol and water and the reaction of this mixture in an adiabatic reactor. This application describes the possibility of converting ethanol into diethyl ether in the first reactor for dehydration in a temperature range going from 200 to 450° C. Neither the use of resin in this first reactor nor the increase in the activity of the catalyst of the reactors following the separation of poisons is mentioned. In addition, this application does not address the problem of maximizing the recovery of heat for the purpose of reducing the energy consumption of the process.

The patent WO 2010/060981 describes a solution for pretreatment of an ethanol feedstock that is optionally biosourced before its passage into a reactor that contains an acid catalyst. It can be applied in particular to the dehydration of ethanol into ethylene. The purpose of the pretreatment described in this patent is to limit the inhibition or the poisoning of the catalyst by components contained in the ethanol feedstock. The pretreatment can be done using an absorbent or using a hydrogenation catalyst that makes it possible to convert at least a portion of the components that are harmful for the catalyst into neutral components. This patent does not describe the possibility of using a catalyst or a resin in the pretreatment that leads to the dehydration of ethanol into diethyl ether.

The patent JP11043452A describes a solution for pretreatment of an ethanol feedstock that uses an ion-exchange resin, kaolin, or a zeolite for reducing the amount of basic nitrogen-containing compound below 10 ppm by weight. The formation or the effect of diethyl ether on the feedstock evaporation is not mentioned.

One objective of the invention is to provide a process for dehydration of ethanol into ethylene comprising a stage for pretreatment of the ethanol feedstock using an acidic solid so as to limit the amount of organic nitrogen, which reduces the service life of the catalyst, and to partially convert ethanol into DEE.

SUMMARY AND ADVANTAGE OF THE INVENTION

The invention describes a process for dehydration of an ethanol feedstock into ethylene comprising a pretreatment stage. Said pretreatment stage reduces the level of organic or basic nitrogen contained in said feedstock and converts a fraction of the ethanol into DEE.

Said invention offers the advantage relative to the processes of the prior art of increasing the cycle time of the catalyst for dehydration of ethanol by trapping the cationic or anionic impurities; the basic, complexing, chelating impurities; or the inorganic or organic impurities, such as, for example, the nitrogen that is present in the feedstock in basic form, for example in the form of ammonia and/or organic and basic radicals, for example in the form of amine, amide, imine or nitrile during the pretreatment stage. The trapping of nitrogen-containing compounds has the result in particular of improving the activity of the acid catalysts used in dehydration.

In a preferred arrangement comprising a compression of the evaporated feedstock, this invention offers the advantage, relative to the processes of the prior art, of maximizing the heat exchange between the feedstock and the effluent obtained from the last reactor for dehydration, i.e., of exchanging the entire evaporation enthalpy of the feedstock and the majority of the condensation enthalpy of said effluent due to the introduction of the feedstock in the stage a) for evaporation at a pressure that is lower than the pressure of the effluent exiting the last reactor.

The applicant discovered that, surprisingly enough, said pretreatment stage conducted under the operating conditions according to the invention ended in the partial conversion of ethanol into DEE and made it possible to reduce significantly the energy consumption of the ethylene production.

DESCRIPTION OF THE INVENTION

The invention relates to a process for dehydration of an ethanol feedstock into ethylene comprising at least the stages:
a) A stage for pretreatment of the ethanol feedstock on an acidic solid operating at a temperature of between 100 and 130° C. in such a way as to produce a pretreated ethanol feedstock,
b) A stage for evaporation of an evaporation feedstock comprising said ethanol feedstock that is pretreated in a heat exchanger, with said evaporation feedstock being introduced into said evaporation stage at a pressure of between 0.1 and 2.5 MPa in such a way as to produce an evaporated feedstock,
c) A stage for superheating said evaporated feedstock in such a way as to bring it to an inlet temperature that is compatible with the temperature of the dehydration reaction,
d) A stage for dehydration of said feedstock that is obtained from stage c) in at least one adiabatic reactor that contains at least one dehydration catalyst and in which the dehydration reaction takes place, operating at an inlet temperature of between 350 and 550° C. and at an inlet pressure of between 0.3 and 1.8 MPa.

Feedstock

In accordance with the invention, the feedstock that is treated in the dehydration process is an ethanol feedstock. Said ethanol feedstock is advantageously a concentrated ethanol feedstock. Concentrated ethanol feedstock is defined as an ethanol feedstock that comprises a percent by mass of ethanol that is greater than or equal to 35% by weight. Preferably, said concentrated ethanol feedstock comprises a percent by mass of ethanol of between 35 and 99.9% by weight.

The ethanol feedstock that comprises less than 35% by weight of ethanol can be concentrated by any means known to one skilled in the art, for example by distillation, by absorption, and by pervaporation.

Said ethanol feedstock also advantageously comprises, in addition to water, a content of alcohols other than ethanol, such as, for example, methanol, butanol and/or isopentanol that is less than 10% by weight, and preferably less than 5% by weight, a content of oxidized compounds other than the alcohols such as, for example, ethers, acids, ketones, aldehydes, and/or esters that are less than 1% by weight, and a nitrogen and sulfur content, organic and mineral, of less than 0.5% by weight, with the percentages by weight being expressed relative to the total mass of said feedstock.

The ethanol feedstock that is treated in the process according to the invention is optionally obtained by a process for the synthesis of alcohol from fossil resources, such as, for example, from carbon, natural gas, or carbon waste.

Said feedstock can also advantageously come from non-fossil resources. Preferably, the ethanol feedstock that is treated in the process according to the invention is an ethanol feedstock that is produced from a renewable source that is obtained from the biomass, often called "bioethanol." The bioethanol is a feedstock that is produced by biological means, preferably by fermentation of sugars obtained from, for example, sugar-producing crops such as sugarcane (saccharose, glucose, fructose and sucrose), beet scraps, or else amylase plants (starch), or lignocellulosic biomass or hydrolyzed cellulose (majority glucose and xylose, galactose), containing variable amounts of water.

For a more complete description of conventional fermentation processes, it is possible to refer to the work 'Les Biocarburants, État des lieux, perspectives et enjeux du développement [The Biofuels: Assessment, Perspectives and Development Issues], Daniel Ballerini, Editions Technip.'

Said feedstock can also advantageously be obtained from synthesis gas.

Said feedstock can also advantageously be obtained by hydrogenation of the corresponding acids or esters. In this case, the acetic acid or the acetic esters are advantageously hydrogenated using hydrogen in ethanol. The acetic acid can advantageously be obtained by carbonylation of methanol or by fermentation of carbohydrates.

Preferably, the ethanol feedstock that is treated in the process according to the invention is an ethanol feedstock that is produced from a renewable source that is obtained from the biomass.

Pretreatment Stage a)

In accordance with the invention, the ethanol feedstock undergoes a pretreatment stage a) in such a way as to produce a pretreated ethanol feedstock. Said pretreatment stage makes it possible to eliminate the nitrogen-containing compounds that are present in said feedstock in such a way as to limit the deactivation of the dehydration catalyst that is placed downstream.

Said pretreatment stage a) is implemented on an acidic solid, preferably an acidic resin, and at a temperature of between 100 and 130° C., preferably between 110° C. and 130° C.

The ethanol feedstock is advantageously heated to the temperature of the pretreatment stage a) in a heat exchanger, owing to a heat exchange with a heat source that is external to the process, for example by direct heating (for example in a furnace) or any other technique that is known to one skilled in the art.

Said pretreatment stage a) makes it possible to eliminate the impurities, basic and/or organic, and the cationic radicals so as to obtain a pretreated ethanol feedstock that responds to the level of impurities that are compatible with the dehydration catalyst.

The pretreatment on the acidic solid under the operating conditions according to the invention makes it possible to convert between 3% by weight and 20% by weight, preferably between 8 and 12% by weight, of the ethanol that is present in said feedstock into DEE, with the percentage by weight being determined relative to the total weight of ethanol that is present in said feedstock entering the pretreatment stage a).

The acidic solid comprises all of the acidic solids that are known by one skilled in the art: alumina-silicas, acidic clays, zeolites, sulfated zirconia, acidic resins, etc. The main thing is for the acidic solid to have a high exchange capacity for capturing the basic and cationic radicals as much as possible and an acidity force that is high enough to effect the partial transformation of ethanol into DEE.

Acidic solids that are commonly available commercially are the clays that are treated with acids to make them acidic (such as montmorillonite) and zeolites, having a silica to alumina ratio in the crystalline network of 2.5 to 100 mol. The acidic resins comprise sulfonic groups, grafted on an organic substrate that consists of aromatic and/or haloaliphatic chains. Preferably, the acidic solids have an exchange capacity of at least 0.1 mmol of $H^+$ equivalent per gram.

The acidic resin comprises acidic sulfonic groups and is prepared by polymerization or copolymerization of aromatic vinyl groups followed by a sulfonation, with said aromatic vinyl groups being selected from among styrene, vinyl toluene, vinyl naphthalene, vinyl ethyl benzene, methyl styrene, vinyl chlorobenzene and vinyl xylene, with said resin having a cross-linking level of between 20 and 35%, preferably between 25 and 35%, and in a preferred manner equal to 30%, and an acidic force metered by potentiometry during neutralization by a KOH solution of 0.2 to 6 mmol of $H^+$ equivalent per gram and preferably between 0.2 and 2.5 mmol of $H^+$ equivalent per gram.

Said acidic ion-exchange resin contains between 1 and 2 terminal sulfonic groups per aromatic group. Its size is between 0.15 and 1.5 mm. Size of the resin is defined as the diameter of the smallest sphere that encompasses the resin particle. The resin size classes are measured by sieving on suitable sieves according to a technique that is known to one skilled in the art.

A preferred resin is a resin that consists of copolymers of aromatic monovinyl and aromatic polyvinyl, and in a very preferred manner, copolymers of divinyl benzene and polystyrene having a cross-linking level of between 20 and 45%, preferably between 30 and 40%, and in a preferred manner equal to 35%, and an acidic force, representing the number of active sites of said resin, metered by potentiometry during the neutralization by a KOH solution, encompassed between 1 and 10 mmol of $H^+$ equivalent per gram and preferably between 3.5 and 6 mmol of $H^+$ equivalent per gram. For example, the resin is a TA801 resin sold by the Axens Company.

The acidic solids can be regenerated from time to time once the exchange capacity is nearly saturated by the adsorption of basic and cationic radicals in situ or ex situ. In the case of inorganic acidic solids such as clays and zeolites, the regeneration can consist of a simple heating at high temperature so as to desorb the basic radicals in the presence of a stream that is inert or that contains oxygen. The cations can be removed by ion exchange. The acidic resins can be regenerated by ion exchange, typically by a treatment with an acid in the liquid phase. The acidic solids can also be used once until they are saturated and replaced by a virgin solid.

The acidic solid can be used by itself or mixed with other types of acidic solids. Mixtures of different acidic solids or sequences of acidic solids can be used so as to optimize the capacity of adsorbing the basic and cationic radicals and the capacity of partially transforming the ethanol into DEE.

The pretreatment described above can advantageously be completed by a pretreatment using an anion exchange resin. This resin can be, for example, a resin that is loaded with sodium or trimethylammonium characterized by an exchange capacity measured in $mg/(OH^-)/liter$. This resin can be, for example, Amberlite IRN78 resin. This additional resin makes it possible to retain the sulfate ions $SO_4^{2-}$ so as to extend the life of the catalyst.

Evaporation Stage b)

The feedstock that comprises said pretreated ethanol feedstock is called the evaporation feedstock. Said evaporation feedstock also advantageously comprises a stream of water that is recycled according to the recycling stage e) or a stream of water external to the process. In this case, the ratio by mass of the stream of water, which is recycled or external to the process, to the pretreated ethanol stream is advantageously between 1 and 4, for the purpose of lowering the partial pressures of ethanol in the dehydration reactor(s) and of making the process more selective for ethylene.

In accordance with the invention, the dehydration process comprises a stage b) for evaporating said evaporation feedstock in such a way as to produce an evaporated feedstock. Said evaporation is carried out using a heat exchange in a heat exchanger with a heat source that can be a stream that is internal or external to the process, or by direct heating (for example, in a furnace), or any other technique that is known to one skilled in the art.

Surprisingly enough, at a given pressure, the evaporation temperature of the evaporation feedstock is lowered relative to that of a feedstock that is obtained by a scheme that would not include the pretreatment stage a).

Said evaporation feedstock is introduced into said stage b) for evaporation at a pressure of between 0.1 and 2.5 MPa.

Optional Compression Stage

In a preferred arrangement, said evaporated feedstock undergoes compression in a compression stage in such a way as to produce a compressed feedstock. Said compression stage is advantageously used in any type of compressor known to one skilled in the art. In particular, the compression stage is advantageously used in a compressor of the radial compressor type with an integrated multiplier or in a compressor that comprises one or more fans with a radial wheel arranged in series without intermediate cooling or in a compressor of the volumetric type with or without lubrication.

The optional compression stage makes it possible to produce a heat pump that is integrated with said process, using the streams obtained from the process, by making it possible to evaporate the evaporation feedstock of stage b) by heat exchange with the effluent that is obtained from the dehydration stage d).

In the case where the optional compression stage is carried out, said evaporation feedstock is introduced into said evaporation stage b) at a pressure of between 0.1 and 1.4 MPa, preferably between 0.2 and 0.6 MPa.

The pressure of said feedstock that is compressed at the end of the optional compression stage is advantageously between 0.3 and 1.8 MPa, preferably between 0.5 and 1.3 MPa. The pressure exiting said feedstock is high enough so that the condensation temperature of the effluent that is obtained from the last reactor is higher than the evaporation temperature of the feedstock entering stage b), which is a condition that is necessary to the feasibility of stage b).

Surprisingly enough, at a given pressure, the evaporation temperature of the evaporation feedstock is lowered relative to that of a feedstock that is obtained by a scheme that would not comprise the pretreatment stage a). For a condensation temperature of the effluent from the given dehydration stage d) and a thermal approach that is set in the heat exchanger that makes possible heat exchange between said evaporation feedstock and said effluent from stage d), it is therefore possible to adjust the pressure upstream from stage b) for evaporation at a higher value than what would have been in a scheme that does not comprise the pretreatment stage a). The level of compression that is necessary in the optional compression stage is thus reduced for reaching a given pressure at the end of said stage, reducing the energy consumption of said stage.

The combination of the specific operating conditions of stage b) and of the optional compression stage makes it possible to prevent the supply of coolant external to the process for ensuring the evaporation of said evaporation feedstock by recovering the majority of the latent heat from the aqueous phase of the effluent that is obtained from stage d) for evaporating the evaporation feedstock. Thus, only the streams that are obtained from the process are used.

Superheating Stage c)

Said evaporated feedstock, optionally compressed, is heated in an exchanger of the gas single-phase type, using a heat exchange with any stream that is internal or external to the process, preferably using a heat exchange with the effluent that is obtained from the last adiabatic reactor of stage d). In said exchanger of the gas single-phase type, said feedstock, optionally compressed, is superheated. In the case where the heat exchange is carried out with the effluent that is obtained, in the gaseous state, from the last adiabatic reactor of stage d), the latter is "de-superheated" without being condensed.

In the case where the optional compression stage is carried out, said exchanger of the gas single-phase type is an exchanger from a technology that is known to one skilled in the art and that makes it possible to minimize the pressure drops while having a large exchange surface. This gas/low-pressure gas exchange induces a low heat flow density through the wall of the exchanger (low transfer coefficient), which makes it necessary to have a large exchange surface. In addition, the pressure drop is to be minimized so as to limit the feedstock of the compressor of the optional compression stage. For example, this exchanger can be an exchanger with pressurized plates in a calender, of the Packinox type supplied by Alfa Laval.

Said evaporated feedstock, optionally compressed, optionally heated in said exchanger of the gas single-phase type, is then introduced into a piece of superheating equipment, preferably a furnace, in such a way as to bring it to an inlet temperature in at least one adiabatic reactor that is compatible with the temperature of the dehydration reaction.

The presence of the pretreatment stage a) makes it possible to increase the activity of the catalyst and to reduce the inlet temperature of the feedstock in the dehydration stage d).

Dehydration Stage d)

In accordance with the invention, said feedstock that is obtained from stage c) undergoes a dehydration stage d) in at least one adiabatic reactor that contains at least one fixed catalyst bed for dehydration and in which the dehydration reaction takes place.

The dehydration stage d) is advantageously carried out in one or two reactors.

In the case where stage d) is used in an adiabatic reactor, said compressed, and optionally heated, feedstock is advantageously introduced into said reactor at an inlet temperature of between 350 and 550° C. and preferably between 400 and 500° C., and at an inlet pressure of between 0.3 and 1.8 MPa, and preferably between 0.4 and 0.8 MPa.

The effluent that is obtained from said adiabatic reactor of stage d) advantageously has a temperature of between 270 and 450° C., and preferably between 340 and 430° C., and an outlet pressure of between 0.2 and 1.6 MPa, and preferably between 0.3 and 0.8 MPa.

In the case where stage d) is used in two adiabatic reactors, said compressed, and optionally heated, feedstock is advantageously introduced into the first reactor at an inlet temperature of between 350 and 550° C., and preferably at a temperature of between 370 and 500° C., and at an inlet pressure of between 0.3 and 1.8 MPa, and preferably between 0.4 and 1.1 MPa.

The effluent that is obtained from the first adiabatic reactor advantageously exits from said first reactor at a temperature of between 270 and 450° C., and preferably between 290 and 390° C., and at a pressure of between 0.3 and 1.7 MPa, and preferably between 0.3 and 1.0 MPa.

Said effluent is then advantageously introduced into a furnace in such a way that the inlet temperature of said effluent in the second adiabatic reactor is between 350 and 550° C. and preferably between 400 and 500° C. Said effluent has an inlet pressure in said second reactor that is advantageously between 0.3 and 1.7 MPa and preferably between 0.3 and 0.9 MPa.

The effluent that is obtained from the second adiabatic reactor exits from said second adiabatic reactor at a temperature that is advantageously between 270 and 450° C., and preferably between 340 and 430° C. The outlet pressure of said effluent that is obtained from the second adiabatic reactor is advantageously between 0.2 and 1.6 MPa and preferably between 0.3 and 0.8 MPa.

The inlet temperature of the reactor(s) can advantageously be gradually increased to prevent the deactivation of the dehydration catalyst.

The dehydration reaction that takes place in at least one adiabatic reactor of stage d) of the process according to the invention is advantageously performed at an hourly speed by weight of between 0.1 and 20 $h^{-1}$, and preferably between 0.5 and 15 $h^{-1}$. The hourly speed by weight is defined as being the ratio of the mass flow rate of the pure ethanol feedstock to the catalyst mass.

The dehydration catalyst used in stage d) is a catalyst that is known to one skilled in the art. Said catalyst is an amorphic acid catalyst, a zeolitic acid catalyst, a catalyst based on alumina-silica, a catalyst based on alumina, or a catalyst based on silica alumina.

Said catalyst is preferably an amorphous acid catalyst or a zeolitic acid catalyst.

In the case where the dehydration catalyst that is used in stage d) is a zeolitic catalyst, said catalyst comprises at least one zeolite that is selected from among the zeolites that have at least openings of pores that contain 8, 10 or 12 oxygen atoms (8 MR, 10 MR or 12 MR). It is actually known to define the size of the pores of the zeolites by the number of oxygen atoms that form the annular cross-section of the channels of the zeolites, called "member ring" or MR in English. In a preferred manner, said zeolitic dehydration catalyst comprises at least one zeolite that has a structural type that is selected from among the structural types MFI, FAU, MOR, FER, SAPO, TON, CHA, EUO, MEL and BEA. Preferably, said zeolitic dehydration catalyst comprises a zeolite of the structural type MFI and in a preferred manner a ZSM-5 zeolite.

The zeolite that is employed in the dehydration catalyst used in stage d) of the process according to the invention can advantageously be modified by dealuminification or desilication according to any method of dealuminification or desilication that is known to one skilled in the art.

The zeolite that is employed in the dehydration catalyst that is used in stage d) of the process according to the invention or the final catalyst can advantageously be modified by an agent of the type to attenuate its total acidity and to improve its hydrothermal resistance properties. Preferably, said zeolite or said catalyst advantageously comprises phosphorus, preferably added in $H_3PO_4$ form followed by a vapor treatment after neutralization of the excess acid by a basic precursor, such as, for example, calcium Ca. In a preferred manner, said zeolite comprises a phosphorus content of between 1 and 4.5% by weight, preferably between 1.5 and 3.1% by weight, relative to the total mass of the catalyst.

Preferably, the dehydration catalyst that is used in stage d) of the process according to the invention is the catalyst that is described in the patent applications WO/2009/098262, WO/2009/098267, WO/2009/098268, or WO/2009/098269.

In the case where the dehydration catalyst that is used in stage d) is an amorphous acid catalyst, said catalyst comprises at least one porous refractory oxide that is selected from among alumina, alumina that is activated by a deposit of mineral acid, and alumina-silica.

Said amorphous or zeolitic dehydration catalyst that is used in stage d) of the process according to the invention can advantageously also comprise at least one oxide-type matrix that is also called a binder. According to the invention, matrix is defined as an amorphous matrix that is crystallized or that comprises amorphous and crystallized parts. Said matrix is advantageously selected from among the elements of the group that is formed by clays (such as, for example, from among the natural clays such as kaolin or bentonite), magnesia, aluminas, silicas, alumina-silicas, aluminates, titanium oxide, boron oxide, zirconia, aluminum phosphates, titanium phosphates, zirconium phosphates, and carbon, used by themselves or in a mixture. Preferably, said matrix is selected from among the elements of the group that is formed by the aluminas, the silicas, and the clays.

Said dehydration catalyst that is used in stage d) of the process according to the invention is advantageously shaped in the form of grains of different shapes and sizes. It is advantageously used in the form of cylindrical or multilobar extrudates such as bilobar, trilobar and multilobar extrudates of straight or twisted shape, but can optionally be manufactured and used in the form of crushed powder, tablets, rings, balls, wheels, or spheres. Preferably, said catalyst is in the form of extrudates.

Said dehydration catalyst that is used in stage d) of the process according to the invention is advantageously employed in at least one reactor, in a fixed bed or in a moving bed.

In stage d) of the process according to the invention, the catalysts that are used and the operating conditions are selected in such a way as to maximize the production of ethylene. The overall dehydration reactions that are implemented in stage d) of the process according to the invention are as follows:

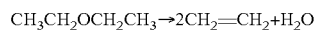

The conversion of the ethanol feedstock in stage d) is greater than 90%, preferably 95%, and in a preferred manner greater than 99%.

A conversion that is less than 90% has the effect of lowering the overall yield of the process, a larger amount of DEE that is not converted into ethylene being lost in the downstream separation stages.

The conversion of the ethanol feedstock is defined, in percentage, by the following formula:

[1−(hourly output mass of ethanol/hourly input mass of ethanol)]×100.

The hourly input and output mass of ethanol is measured conventionally by, for example, chromatography.

Stage d), in which the dehydration reaction takes place, is advantageously carried out in one or two reactors. A preferred reactor is a radial reactor that operates in upward or downward mode. During stage d) of the process according to the invention, the transformation of the feedstock is accompanied by the deactivation of the dehydration catalyst by coking and/or by adsorption of inhibiting compounds. The dehydration catalyst is therefore to periodically undergo a regeneration stage. Preferably, the reactor is used in an alternate regeneration mode, also called a swing reactor, so as to alternate the reaction and regeneration phases of said dehydration catalyst. The objective of this regeneration treatment is to burn the organic deposits as well as the radicals that contain nitrogen and sulfur, contained at the surface and within said dehydration catalyst. The pretreatment stage a) that is implemented in this invention makes it possible to reduce the amount of impurities, basic and organic, as well as the cationic radicals that will alter the service life of the catalyst. The elimination of these radicals thus makes it possible to limit the regeneration number of the catalyst.

Optionally, for example in the case where the evaporation feedstock does not comprise the recycled water stream or the water stream that is external to the process, the number of reactors can be increased so as to compensate for the endothermicity of the reaction by the presence of intermediate furnaces in the progression of the ethanol dehydration reaction.

The regeneration of the dehydration catalyst that is used in said stage d) is advantageously carried out by oxidation of coke and inhibiting compounds under a stream of air or in an air/nitrogen mixture, for example by using a recirculation of the combustion air with or without water so as to dilute oxygen and to control regeneration exothermy. In this case, it is possible to advantageously adjust the content of oxygen entering the reactor by a supply of air. Regeneration takes place at a pressure between atmospheric pressure and the reaction pressure.

The regeneration temperature is advantageously selected between 400 and 600° C.; it can advantageously vary during regeneration. The end of the regeneration is detected when there is no longer oxygen consumption, a sign of the total combustion of the coke.

The effluent that is obtained from the last adiabatic reactor of stage d) is optionally sent into a gas single-phase-type exchanger in which it is "de-superheated" without being condensed by heat exchange with the compressed feedstock that is obtained from the optional compression stage, in which it is superheated.

Said "de-superheated" effluent is then advantageously sent into a second gas/liquid-type exchanger in which it is partially condensed by a heat exchange that is used to evaporate the evaporation feedstock.

Said effluent is then preferably cooled again by heat exchange with the ethanol feedstock during the preheating of the ethanol feedstock.

Purification and Recycling Stage e)

Optionally, the effluent that is obtained from the dehydration stage d) then undergoes a cooling, for example in a gas/liquid separation column.

Preferably, at least a portion of the treated water stream that is obtained from the condensation of the effluent is recycled upstream from the evaporation stage b).

The effluent that is obtained from stage d) then preferably undergoes a compression stage and a purification stage according to means that are known to one skilled in the art. Preferably, these stages make it possible to separate the components that deteriorate the polymerization of the ethylene, in particular acetaldehyde and $CO_2$.

DESCRIPTION OF THE FIGURES

FIG. 1 diagrammatically shows a particular arrangement of the process of dehydration of an ethanol feedstock that implements a pretreatment with a recycling of at least a portion of water treated during stage (e) of the process.

The ethanol feedstock (1) is introduced into a pretreatment zone (a). The pretreated ethanol feedstock (2) is then mixed in the pipe (3) with a portion of the treated water stream that is obtained from the purification zone (f) that is recycled in such a way as to serve as reaction diluent via the pipe (14). This mixture, constituting the evaporation feedstock, is introduced via the pipe (3) into a gas/liquid exchanger E1 in which said mixture undergoes a heat exchange with the effluent that is obtained from the dehydration section (e) that penetrates the exchanger via the pipe (9) in such a way as to produce an evaporated feedstock. The latent heat, also called condensational enthalpy, of the effluent that is obtained from the dehydration zone (e) is used to evaporate the evaporation feedstock, without an external heat supply.

The evaporated feedstock is then sent via the pipe (4) into a compressor C1.

Said evaporated and compressed feedstock is then sent via the pipe (5) into an exchanger E2 of the gas single-phase type, in which said feedstock is heated using a heat exchange with the effluent that is obtained from the dehydration section (e) that is introduced into E2 via the pipe (8). In said exchanger of the gas single-phase type, said evaporated and compressed feedstock is superheated, and the effluent that is obtained, in the gaseous state, from the dehydration section (e) is "de-superheated," without being condensed.

Said evaporated, compressed and heated feedstock in the exchanger of gas single-phase type E2 is then introduced into a furnace H1 via the pipe (6) in such a way as to bring it to an inlet temperature in the dehydration section (e) that is compatible with the temperature of the dehydration reaction.

The effluent that is obtained from the dehydration section (e) then undergoes the two successive exchanges described above in the exchangers E2 and E1 via the pipes (8) and (9).

The effluent that is obtained from the exchanger E1 is sent via the pipe (10) into the purification section (f) where it is separated into at least one effluent that comprises ethylene (12), at least one purge that comprises water (13), at least one effluent that comprises water, and all (optionally a portion) of unreacted ethanol (14), and at least one effluent that comprises light gases (11).

The following examples illustrate the invention without limiting its scope.

EXAMPLES

Example 1: In Accordance with the Invention

Example 1 illustrates a process according to the invention.

The ethanol feedstock under consideration is produced by fermentation of wheat, without extracting glutens, by a dry-milling-type process according to the English term.

Stage a)

The ethanol feedstock is introduced, at a flow rate of 45,664 kg/h, at a temperature of 120° C. and a pressure of 1.15 MPa into a pretreatment resin TA801 so as to eliminate traces of nitrogen-containing compounds. During this pretreatment, a portion of the ethanol is converted into DEE. The characteristics of the crude and pretreated ethanol feedstock are provided in Table 1.

TABLE 1

Characteristics of the Ethanol Feedstock Before and After Pretreatment (Percent by Mass)

| | ETHANOL FEEDSTOCK | ETHANOL AFTER PRETREATMENT |
| --- | --- | --- |
| ETHANOL | 91.2% | 82.1% |
| H20 | 8.7% | 10.5% |
| DEE | 0% | 7.3% |
| NITROGEN-CONTAINING COMPOUNDS | 0.005% | 0.000% |

Stage b)

The evaporation feedstock, constituted by the pretreated ethanol feedstock in a mixture with 141,252 kg/h of treated water and unconverted ethanol that are recycled according to stage (f), is depressurized and introduced into an exchanger E1 at a pressure that is equal to 0.27 MPa. The bubble temperature of this feedstock at this pressure is 127° C., taking into account the presence of DEE. The evaporation feedstock enters into the exchanger E1 at 113° C. and is therefore already evaporated at 8.6% by mass. The pressure entering the exchanger E1 was adjusted in such a way that the thermal approach with the stream that is obtained from the last adiabatic reactor of stage e) is at least 15° C.

In stage b), the majority of the latent heat of the aqueous phase of the effluent that is obtained from the last adiabatic reactor of stage e) is recovered for evaporating the evaporation feedstock, without an external heat supply. Thus, 93.6 MW is exchanged between said evaporation feedstock and said effluent.

Optional Compression Stage

The evaporated feedstock is then compressed in the optional compression stage using a radial compressor with an integrated multiplier in such a way that the pressure of said evaporated feedstock is equal to 0.695 MPa at the end of the compression.

Stage c)

The compressed feedstock is then heated in an exchanger E2 of the gas single-phase type, using a heat exchange with the effluent that is obtained from the adiabatic reactor of stage d). In said exchanger of the gas single-phase type, said compressed feedstock is superheated to a temperature of 405° C., and the effluent that is obtained, in the gaseous state, from the last adiabatic reactor of stage d) is "de-superheated" without being condensed and has a temperature of 253° C.

Said feedstock that is compressed and heated in said exchanger of the gas single-phase type is then introduced into a furnace in such a way as to bring it to an inlet temperature in the first adiabatic reactor of stage d) that is compatible with the temperature of the reaction for dehydration and conversion of DEE into highly endothermic ethylene, i.e., at a temperature of 440° C.

Stage d)

The trapping of nitrogen-containing compounds in the pretreatment stage a) makes it possible to reduce significantly the inlet temperature of the first adiabatic reactor of stage d).

Said compressed and heated feedstock is introduced into the first adiabatic reactor at an inlet pressure of 0.595 MPa. The pressure of the effluent exiting the last adiabatic reactor of stage e) is 0.500 MPa. The dehydration stage d) is performed at an hourly speed by weight of 7 $h^{-1}$.

The adiabatic reactor contains a fixed dehydration catalyst bed, with said catalyst comprising 80% by weight of ZSM-5 zeolite treated with $H_3PO_4$ in such a way that the phosphorus content P is 3% by weight.

The conversion of the ethanol feedstock in stage d) is 95%.

The outlet temperature of the last adiabatic reactor of stage d) is 420° C.

Stage e)

The effluent that is obtained from the last adiabatic reactor of stage d) then undergoes two heat exchanges, described above, and is sent into the section for purification and recycling.

An effluent that comprises ethylene meeting the final specifications is separated. An effluent that comprises water corresponding to the purge of the process is also separated. A stream that contains light gases and impurities is also separated by one or more optionally cryogenic distillation(s).

A stream of water treated in a mixture with a portion of unconverted ethanol is recycled upstream from the evaporation stage b) in the proportions described in stage b).

Information regarding the different streams, in kg/h, is given in Table 2 and Table 3.

TABLE 2

Composition of the Primary Streams (1/2)

| Description of the Stream | | Pretreated Ethanol Feedstock | Stream Entering into Stage (d) | Stream Exiting from Stage (d) | Effluent Comprising Ethylene |
|---|---|---|---|---|---|
| Stream No. Corresponding to the FIGURE | | 2 | 7 | 8 | 12 |
| Total Mass Flow Rate | kg/h | 45,664 | 186,916 | 186,916 | 25,692 |
| Mass Flow Rate, by Components | kg/h | | | | |
| Ethylene | | 0 | 0 | 25,087 | 25,087 |
| Ethane | | 0 | 0 | 8 | 8 |
| C3 | | 0 | 0 | 93 | 93 |
| C4 | | 0 | 0 | 87 | 87 |
| DEE | | 3,352 | 3,352 | 14 | 14 |
| Ethanol | | 37,504 | 39,310 | 2,187 | 151 |
| $H_2O$ | | 4,808 | 143,730 | 158,602 | 198 |
| Oxidized Compounds (Other than Ethanol) | | 0 | 325 | 586 | 42 |
| Other Minority Components | | 0 | 199 | 252 | 12 |

TABLE 3

Composition of the Primary Streams (2/2)

| Description of the Stream | | Effluent That Comprises Water | Recycling of Ethanol and Water | Purged Water | Light Gases |
|---|---|---|---|---|---|
| Stream No. Corresponding to the FIGURE | | 13 | 14 | 13 | 11 |
| Total Mass Flow Rate | kg/h | 161,224 | 141,252 | 19,007 | 965 |
| Mass Flow Rate, By Components | kg/h | | | | |
| Ethylene | | 0 | 0 | 0 | 0 |
| Ethane | | 0 | 0 | 0 | 0 |
| C3 | | 0 | 0 | 0 | 0 |
| C4 | | 0 | 0 | 0 | 0 |
| DEE | | 0 | 0 | 0 | 0 |
| Ethanol | | 2,036 | 1,806 | 3 | 227 |
| $H_2O$ | | 158,404 | 138,922 | 18,987 | 495 |
| Oxidized Compounds (Other than Ethanol) | | 544 | 325 | 6 | 213 |
| Other Minority Components | | 240 | 199 | 11 | 30 |

The compounds C3 and C4 are C3 and C4 hydrocarbon-containing compounds.

The selectivity of the process in terms of ethylene is 99%.

It is calculated in the following way: (Ethylene that is contained in the effluent that comprises ethylene)/(0.61*amount of converted ethanol) where the amount of converted ethanol is the ethanol that is contained in the ethanol feedstock before pretreatment that is subtracted from the ethanol that is contained in the streams of purged water and in the effluent that comprises ethylene. 0.61 g is the maximum amount of ethylene that is obtained by dehydrating 1 g of pure ethanol.

Information on the energy balance of the diagram according to Example 1 in accordance with the invention is given in Table 4:

TABLE 4

Energy Balance

| Energy Exchanged Inside the System | | Energy Provided to the System by an External Supply | | |
|---|---|---|---|---|
| Amount of Heat Exchanged in the First Exchanger (E1) | Amount of Heat Exchanged in the Second Exchanger (E2) | Amount of Heat Exchanged in the Furnace | Electricity Required for Compression | Amount of Heat Extracted in the Gas/Liquid Separation Column |
| MW | MW | MW | MW | MW |
| 93.6 | 18.32 | 10.4 | 10.9 | 22.53 |

The estimation of the primary energy consumption was carried out by using the following bases:
Effectiveness of 0.8 on the furnaces
Effectiveness of 0.375 on the production of electricity The diagram according to Example 1 in accordance with the invention has an equivalent primary energy consumption or a specific consumption of 6.0 GJ equivalent per ton of ethylene that is produced.

Example 2: Comparison

Example 2 illustrates a process in which the pretreatment stage has not taken place. The ethanol is not converted into DEE, and the process begins in stage b).
Stage b)

The evaporation feedstock, constituted by the non-pretreated ethanol feedstock in a mixture with 141,258 kg/h of treated water and unconverted ethanol that are recycled according to stage e), is introduced, at a flow rate of 186,922 kg/h, into the exchanger E1 at a pressure that is equal to 0.24 MPa and at a temperature of 120° C.

Relative to Example 1, the pressure was lowered by 0.03 MPa. Without the presence of DEE, the bubble temperature of the evaporation feedstock at 0.27 MPa is 115° C. (127° C. in Example 1). The inlet pressure is modified by 0.03 MPa in such a way as to preserve a minimum thermal approach of 15° C. with the effluent that is obtained from the last adiabatic reactor of stage d).

In stage c), the majority of the latent heat of the aqueous phase of the effluent that is obtained from the adiabatic reactor of stage d) is recovered for evaporating the evaporation feedstock, without a supply of external heat. Thus, 98 MW is exchanged between the evaporation feedstock and the effluent from the reactor.
Optional Compression Stage The evaporated feedstock is then compressed in the optional compression stage using a radial compressor with an integrated multiplier in such a way that the pressure of said evaporated feedstock at the end of the compression is equal to 0.695 MPa.
Stage c)

The compressed feedstock is then heated in an exchanger E2 of the gas single-phase type, using a heat exchange with the effluent that is obtained from the last adiabatic reactor of stage d). In said gas single-phase-type exchanger, said compressed feedstock is superheated to a temperature of 405° C., and the effluent that is obtained, in the gaseous state, from the last adiabatic reactor of stage d) is "desuperheated" without being condensed and has a temperature of 269° C.
Stage d)

Said compressed and heated feedstock in said gas single-phase-type exchanger is then introduced into a furnace in such a way as to bring it to an inlet temperature in the first adiabatic reactor of stage d) that is compatible with the temperature of the dehydration reaction, i.e., to a temperature of 470° C. The outlet temperature of the last adiabatic reactor of stage d) is 420° C.

Said compressed and heated feedstock is introduced into the adiabatic reactor at an inlet pressure of 0.595 MPa. The pressure of the effluent exiting the last adiabatic reactor of stage d) is 0.500 MPa. The dehydration stage d) is performed at an hourly speed by weight of 7 $h^{-1}$.

The conversion of the ethanol feedstock in stage d) is 95%.
Stage e)

The effluent that is obtained from the last adiabatic reactor of stage d) then undergoes the two heat exchanges described above and is sent into the section for purification and recycling.

An effluent that comprises ethylene meeting the final specifications is separated. An effluent that comprises water corresponding to the purge of the process is also separated.

A stream that contains light gases and impurities is also separated by one or more optionally cryogenic distillation(s).

A stream of treated water in a mixture with a portion of unconverted ethanol is recycled upstream from the evaporation stage b) in the proportions described in stage b).

Information regarding the different streams, in kg/h, is given in Table 5 and Table 6.

TABLE 5

Composition of the Primary Streams (1/2)

| Description of the Stream | | Ethanol Feedstock | Stream Entering into R1 | Stream Exiting from R2 | Effluent Comprising Ethylene |
|---|---|---|---|---|---|
| Stream No. Corresponding to the FIGURE | | 2 | 7 | 8 | 12 |
| Total Mass Flow Rate | kg/h | 45,664 | 186,922 | 186,922 | 25,964 |
| Mass Flow Rate by Components | kg/h | | | | |
| Ethylene | | 0 | 0 | 25,087 | 25,087 |
| Ethane | | 0 | 0 | 8 | 8 |
| C3 | | 0 | 0 | 93 | 93 |
| C4 | | 0 | 0 | 87 | 87 |
| DEE | | 0 | 0 | 14 | 14 |
| Ethanol | | 41,671 | 43,496 | 2,187 | 151 |
| $H_2O$ | | 3,993 | 142,947 | 158,602 | 311 |
| Oxidized Compounds (Other than Ethanol) | | 0 | 413 | 586 | 62 |
| Other Minority Components | | 0 | 66 | 258 | 151 |

TABLE 6

Composition of the Primary Streams (1/2 [sic])

| Description of the Stream | | Effluent That Comprises Water | Recycling of Ethanol and Water | Purged Water | Light Gases |
|---|---|---|---|---|---|
| Stream No. Corresponding to the FIGURE | | 13 | 14 | 13 | 11 |
| Total Mass Flow Rate | kg/h | 160,958 | 141,258 | 19,007 | 693 |
| Mass Flow Rate, By Components | kg/h | | | | |
| Ethylene | | 0 | 0 | 0 | 0 |
| Ethane | | 0 | 0 | 0 | 0 |
| C3 | | 0 | 0 | 0 | 0 |
| C4 | | 0 | 0 | 0 | 0 |
| DEE | | 0 | 0 | 0 | 0 |
| Ethanol | | 2,036 | 1,825 | 3 | 208 |
| $H_2O$ | | 158,291 | 138,954 | 18,987 | 350 |
| Oxidized Compounds (Other than Ethanol) | | 524 | 413 | 6 | 105 |
| Other Minority Components | | 107 | 66 | 11 | 30 |

The compounds C3 and C4 are C3 and C4 hydrocarbon-containing compounds.

The selectivity of the process in terms of ethylene is 99%.

Information regarding the energy balance of the diagram according to Example 2 is given in Table 7.

TABLE 7

Energy Balance

| Energy Exchanged Inside the System | | | Energy Provided to the System by an External Supply | |
|---|---|---|---|---|
| Amount of Heat Exchanged in the First Exchanger (E1) | Amount of Heat Exchanged in the Second Exchanger (E2) | Amount of Heat Exchanged in the First Furnace | Electricity Required for Compression | Amount of Heat Extracted on the Gas/Liquid Separation Column |
| MW | MW | MW | MW | MW |
| 93.8 | 17.1 | 13.9 | 12.4 | 26.7 |

The diagram according to Example 2 for comparison with the invention has an equivalent primary energy consumption or specific consumption of 7.23 GJ equivalent per ton of ethylene produced.

Without pretreatment, the primary energy consumption therefore increases by 1.2 GJ equivalent per ton of ethylene that is produced.

The invention claimed is:

1. A process for dehydration of an ethanol feedstock into ethylene comprising at least the stages:
   a) pretreating the ethanol feedstock on an acidic solid operating at a temperature of between 100 and 130° C. in such a way as to produce a pretreated ethanol feedstock,
      wherein from 3% to 20% by weight of the ethanol that is present in said feedstock is converted into diethyl ether,
   b) evaporating an evaporation feedstock comprising said ethanol feedstock that is pretreated in a heat exchanger, with said evaporation feedstock being introduced into said evaporation stage at a pressure of between 0.1 and 2.5 MPa in such a way as to produce an evaporated feedstock,
   c) superheating said evaporated feedstock in such a way as to bring it to an inlet temperature that is compatible with the temperature of the dehydration reaction and,
   d) dehydrating said feedstock that is obtained from stage c) in at least one adiabatic reactor that contains at least one dehydration catalyst and in which the dehydration reaction takes place, operating at an inlet temperature of between 350 and 550° C. and at an inlet pressure of between 0.3 and 1.8 MPa.

2. The process according to claim 1, wherein said ethanol feedstock is an ethanol feedstock that is produced from a renewable source that is obtained from biomass.

3. The process according to claim 1, wherein said evaporation feedstock is introduced into said evaporation stage b) at a pressure of between 0.1 and 1.4 MPa and comprising a compression stage of said feedstock that is evaporated prior to said superheating stage c).

4. The process according to claim 3, wherein the pressure of the compressed feedstock is between 0.3 and 1.8 MPa.

5. The process according to claim 1, wherein said evaporated feedstock, optionally compressed, is heated in an exchanger of the gas single phase type, using a heat exchange with the effluent that is obtained from the last adiabatic reactor of stage d).

6. The process according to claim 1, wherein the effluent that is obtained from the last adiabatic reactor of stage d) has exiting the last adiabatic reactor of stage d) a temperature of between 270 and 450° C.

7. The process according to claim 1, wherein the effluent that is obtained from the last adiabatic reactor of stage d) has exiting from the last adiabatic reactor of stage d)—a pressure of between 0.2 and 1.6 MPa.

8. The process according to claim 1, wherein the dehydration stage d) is carried out in one or two reactors.

9. The process according to claim 1, wherein said dehydration catalyst that is used in stage d) is an amorphous acid catalyst or a zeolitic acid catalyst.

10. The process according to claim 1, wherein said ethanol feedstock is a concentrated ethanol feedstock, i.e., an ethanol feedstock that comprises a percent by mass of ethanol that is greater than or equal to 35% by weight.

11. The process according to claim 10, wherein said concentrated ethanol feedstock comprises a percent by mass of ethanol that is between 35 and 99.9% by weight.

12. The process according to claim 1, wherein the pretreatment stage a) is completed by a pretreatment using an anion exchange resin.

13. The process of claim 1, wherein the inlet temperature is between 350 and 550° C.

14. The process of claim 1, wherein from 8% to 12% by weight of the ethanol that is present in said feedstock is converted into diethyl ether from the stage for pretreatment.

* * * * *